Feb. 26, 1957 C. MALLERIN Plant Pat. 1,572
ROSÉ PLANT
Filed May 16, 1956
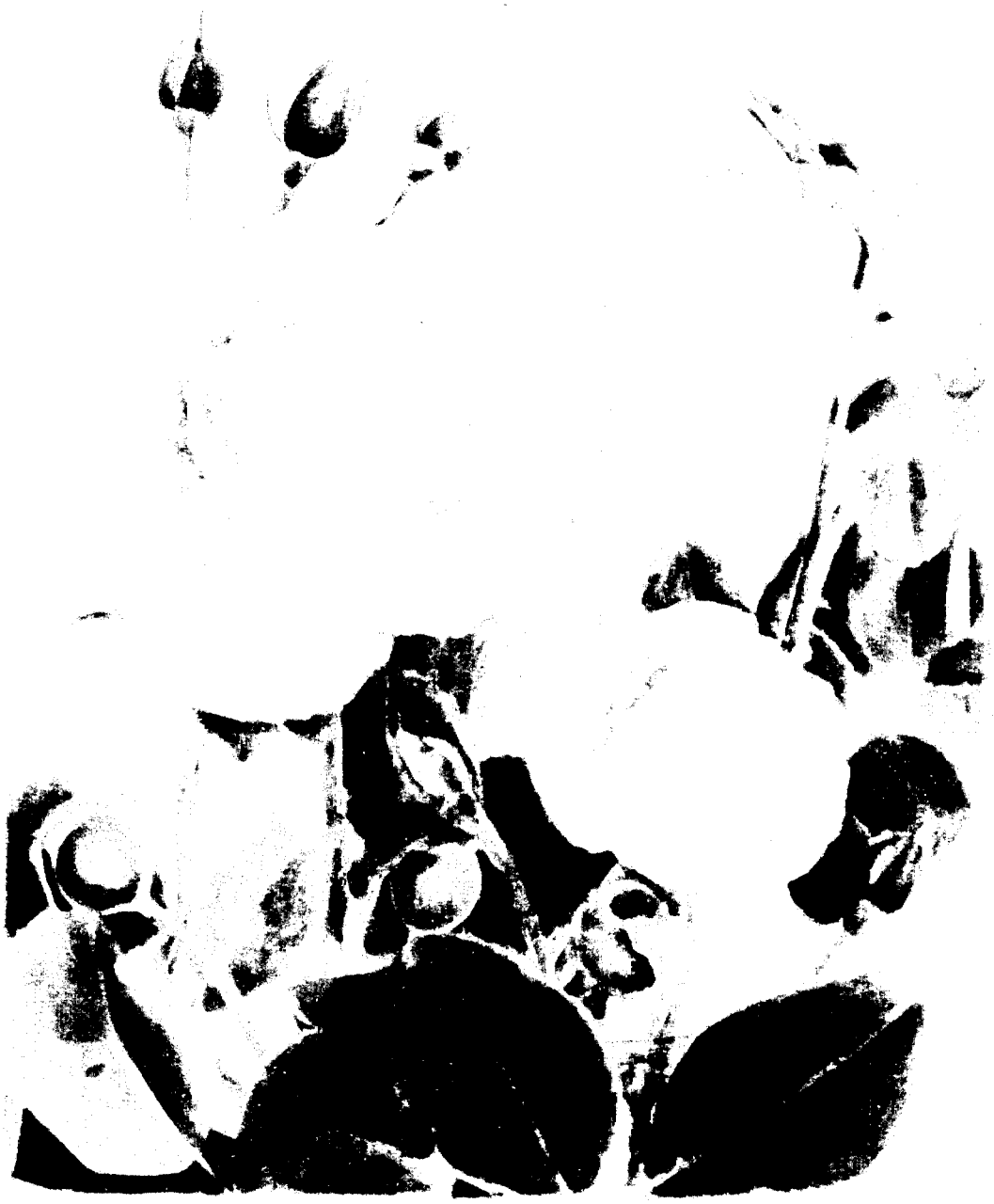
Inventor.
Charles Mallerin
By: Robbins & Robb
Attorneys.

United States Patent Office

Plant Pat. 1,572

Patented Feb. 26, 1957

1,572

ROSE PLANT

Charles Mallerin, Varces, Allieres et Risset, France, assignor to The Conard-Pyle Company, West Grove, Pa., a corporation of Pennsylvania Application May 16, 1956, Serial No. 585,372

1 Claim. (Cl. 47—61)

The present invention relates to a new and distinct variety of rose plant of the hybrid polyantha class, which was originated by me by crossing the variety "Olga" (unpatented) with the variety "Fashion" (Plant Patent No. 789).

The parent variety "Olga" is one which was originated by crossing the variety "Holstein" (Plant Patent No. 395) × "Orange Triumph" (unpatented), and is primarily characterized by its orange-pink colored flowers, but the flowers are somewhat too single and too small, and hence that variety has not been entirely satisfactory as a commercially marketable rose. It was therefore my primary objective in crossing "Olga" with "Fashion" to preserve the remarkable vegetative characteristics of "Holstein" which were inherited in the variety "Olga," while at the same time improving the form and the color of the blooms of "Olga." This objective has been fully achieved, as evidenced by the following characteristics which are dominant in my new variety which is the subject of this application:

(1) An excellent, well-branched and balanced habit of growth which is very vigorous, yet at the same time remains of medium height;

(2) The clean, abundant, well-spaced foliage which is unusually resistant to blackspot and mildew; and (3) The abundance, good form and vivid Signal Red general color tonality of the blooms.

Asexual reproduction of my new variety by budding, as performed by me in France, and as performed on my behalf at West Grove, Pennsylvania, U. S. A., shows that the foregoing characteristics and distinctions of the new variety come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; outdoor; seedling; for cut flowers and for garden decoration.
Class: Hybrid polyantha.
Breeding: Seedling.
*Seed parent.*—"Olga."
*Pollen parent.*—"Fashion."
Propagation: Holds its distinguishing characteristics through succeeding propagations by budding.

*Flower*

Locality where grown and observed: West Grove, Pennsylvania, U. S. A.
Flowers borne: Several to stem; in regular pyramidal clusters; on stems of medium length and normal strength.

Quantity of bloom: Abundant, outdoors.
Continuity: Continuous.
Fragrance: Moderate. Nature—nutty.
Bud:
*Peduncle.*—Medium length; medium caliper; erect; medium rough; with medium number of brown hairs. Color—green.
*Before calyx breaks.*—Size—Medium. Form—Medium length; ovoid; with a conspicuous neck; with foliaceous appendages on the surface of the bud; with slender, entire, bristle-like foliaceous parts extending beyond the tip of the bud equal to ¼ or more of its length.
*As calyx breaks.*—Color—Cardinal Red, Plate 822, sometimes showing areas of Currant Red, Plate 821/3.
*As first petal opens.*—Size—Medium. Form—Ovoid. Color: outside—Currant Red, Plate 821/2; inside—Iridescent Signal Red, Plate 719, sometimes with a White vein extending down the center of the petal.
*Opening.*—Opens up well; is retarded from opening by cold weather.
Bloom:
*Size (when fully open).*—From 2¾ inches to 3 inches.
*Petalage.*—Double; from 23 to 28 petals; arranged regularly.
*Form.*—Globular at first, but becoming open; petals being at first relatively flat in longitudinal section, but later becoming slighty rolled outward at maturity.
Petals:
*Texture.*—Medium thickness; leathery. Inside—velvety. Outside—satiny.
*Shape.*—Outer—obovate, with 2 or 3 notches. Intermediate—obovate, with 2 or 3 notches. Inner—obovate, but generally with no notches.

This description of a newly opened flower was made from a rose grown outdoors in the early part of September, at West Grove, Pennsylvania, U. S. A.:

*Color.*—Outer petal:—outside surface—Carmine, Plate 21, shading to a small area of Magenta, Plate 27 at base; inside surface—Iridescent Geranium Lake, Plate 20, tinged at base of petal with Mallow Purple, Plate 030/1. Intermediate petal: outside surface—Mainly Carmine, Plate 21/1, surrounded by Carmine, Plate 21 at margin; inside surface—Iridescent Signal Red, Plate 719. Inner petal: outside surface—Carmine, Plate 21, usually with streaks of Phlox Purple, Plate 632 radiating from base of petal; inside surface—Iridescent Scarlet, Plate 19.

This description was made from a rose that was open for 3 days outdoors in the month of Spetember, at West Grove, Pennsylvania, U. S. A.:

*Color.*—Outer petal: outside surface—Rose Madder, Plate 23/1; inside surface—Carmine, Plate 21/1, with margin of Neyron Rose, Plate 623 at base of petal. Inner petal: outside surface—Rose Madder, Plate 23/1, occasionally with a streak of Magenta, Plate 27/1; inside surface—Geranium Lake, Plate 20/1 at outer margin of petal, shading to Neyron Rose, Plate 623 at base of petal.
*General color effect.*—Newly opened flower—Signal Red, Plate 719. 3-days open—Carmine, Plate 21/1.
*Behavior.*—Drop off cleanly; shows tendency to slightly blue as result of cold weather.
*Flower longevity.*—On bush in garden—3 or 4 days in September. Cut roses grown outdoors and kept at living-room temperatures—4 days in September.

*Reproduction organs*

Stamens: Many; arranged regularly about pistils.
Filaments: Many; most with anthers; medium length. Color—Tyrian Rose, Plate 24/2.
Anthers: All open at once; medium size; seldom fused with a petaloid. Color—reddish.
Pollen: Moderate. Color—Lemon Yellow, Plate 4.
Pistils: Medium number.
Styles: Uneven; medium length; medium thinness: bunched.
Stigma: Color—White.
Ovaries: All enclosed in calyx.
Hips: Medium length; ovoid; with inconspicuous neck; smooth; walls medium thickness and fleshy. Color—green.
Sepals: Permanent; medium length; spear-shaped.
Seeds: Medium number; medium size.

*Plant*

Foliage:

*Leaves.*—Compound of 5 to 7 leaflets; normal abundance; medium size; leathery.

*Leaflets.*—Shape—oval, with apex mucronate. Base—obtuse. Margin—simply serrate.

*Color.*—Mature: upper surface—Parsley Green, Plate 00962; under surface—Willow Green, Plate 000862/1. Young: upper surface—Lettuce Green, Plate 861, overcast with Oxblood Red, Plate 00823/1; under surface—generally Oxblood Red, Plate 00823.

*Rachis (the supporting stem of the compound leaf).*—Medium caliper. Upper side—grooved; hairy.

Under side—moderately thorny.

*Stipules.*—Medium length; moderately narrow; with short points turning out at an angle of 45°.

*Disease resistance.*—Unusually resistant to mildew and blackspot, as determined by comparison with other varieties grown under comparable cultural conditions at West Grove, Pennsylvania, U. S. A.

Growth:

*Habit.*—Bushy; much-branched.

*Growth.*—Free.

*Canes.*—Medium caliper.

*Main stems.*—Color—Lettuce Green, Plate 861. Thorns—several; medium length; hooked downward; with oval base of medium length. Prickles—few; color—sometimes green but sometimes bronze. Hairs—none.

*Branches.*—Color—Lettuce Green, Plate 861. Thorns—several; medium length; hooked downward; with short, oval base. Prickles—few; color—bronze. Hairs—none.

*New shoots.*—Color—Pod Green, Plate 061. Thorns—many; medium length; hooked downward; with oval base of medium length. Prickles—several; color—variable reddish. Hairs—none.

I claim:

A new and distinct variety of rose plant of the hybrid polyantha class, substantially as herein shown and described, characterized particularly as to novelty by its well-branched, balanced, very vigorous but compact and medium tall habits of growth, its clean, abundant, well-spaced foliage which is unusually resistant to blackspot and mildew, and the abundance, good form and vivid Signal Red general color tonality of its blooms.

No references cited.